United States Patent
Lunner et al.

(10) Patent No.: US 9,560,458 B2
(45) Date of Patent: Jan. 31, 2017

(54) CONFIGURABLE HEARING INSTRUMENT

(71) Applicant: OTICON A/S, Smørum (DK)

(72) Inventors: Thomas Lunner, Smørum (DK); Niels Henrik Pontoppidan, Smørum (DK)

(73) Assignee: OTICON A/S, Smorum (DK)

( * ) Notice: Subject to any disclaimer, the term of this patent is extended or adjusted under 35 U.S.C. 154(b) by 346 days.

(21) Appl. No.: 14/103,399

(22) Filed: Dec. 11, 2013

(65) Prior Publication Data

US 2014/0169596 A1 Jun. 19, 2014

Related U.S. Application Data

(60) Provisional application No. 61/737,133, filed on Dec. 14, 2012.

(30) Foreign Application Priority Data

Dec. 14, 2012 (EP) .................................. 12197265

(51) Int. Cl.
*H04R 25/00* (2006.01)
*A61B 5/048* (2006.01)
*A61B 5/0476* (2006.01)

(52) U.S. Cl.
CPC ............. *H04R 25/70* (2013.01); *A61B 5/0476* (2013.01); *A61B 5/048* (2013.01); *H04R 2225/41* (2013.01)

(58) Field of Classification Search
CPC ..... A61B 5/0476; A61B 5/0478; A61B 5/048; A61B 5/0482; A61B 5/0484; A61B 5/04842; A61B 5/04845; A61B 5/04847
See application file for complete search history.

(56) References Cited

U.S. PATENT DOCUMENTS

| | | | | |
|---|---|---|---|---|
| 6,330,339 B1* | 12/2001 | Ishige | .................. | H04R 25/502 |
| | | | | 381/312 |
| 8,284,968 B2* | 10/2012 | Schumaier | ............. | H04R 25/70 |
| | | | | 312/314 |
| 9,025,800 B2* | 5/2015 | Kidmose | ............ | A61B 5/04845 |
| | | | | 381/312 |
| 9,313,585 B2* | 4/2016 | Lunner | ................ | H04R 25/505 |
| 2005/0137494 A1* | 6/2005 | Viertio-Oja | ............ | A61B 5/048 |
| | | | | 600/544 |
| 2008/0285780 A1* | 11/2008 | Aarts | ..................... | H04R 25/70 |
| | | | | 381/312 |
| 2009/0112281 A1* | 4/2009 | Miyazawa | .......... | A61N 1/36071 |
| | | | | 607/46 |
| 2009/0259136 A1* | 10/2009 | Schieb | ................. | A61B 5/4821 |
| | | | | 600/544 |

(Continued)

OTHER PUBLICATIONS

European Search Report issued in 12197265.7-1901 completed on Apr. 17, 2013.

*Primary Examiner* — Meredith Weare
(74) *Attorney, Agent, or Firm* — Birch, Stewart, Kolasch & Birch, LLP (57) ABSTRACT

A system for operating a hearing instrument is disclosed. The system comprises one or more electrodes for measuring the brain wave signals of a user wearing a hearing instrument. The electrodes are placed on the scalp of the user. Based on the measured brain wave signals, a detecting unit is configured to detect a relaxation state of the hearing instrument. A controller sets the hearing instrument to a relaxation mode setting in response to the detection of the relaxation state of the user.

20 Claims, 4 Drawing Sheets

(56) References Cited

U.S. PATENT DOCUMENTS

| | | | | |
|---|---|---|---|---|
| 2010/0160714 A1* | 6/2010 | Chua | ............... | H04R 25/558 |
| | | | | 600/25 |
| 2010/0196861 A1* | 8/2010 | Lunner | ............... | H04R 25/505 |
| | | | | 434/112 |
| 2011/0251583 A1* | 10/2011 | Miyazawa | ......... | A61N 1/36071 |
| | | | | 604/503 |
| 2012/0108998 A1* | 5/2012 | Molnar | ............ | A61B 5/04014 |
| | | | | 600/545 |
| 2012/0123290 A1* | 5/2012 | Kidmose | ............ | A61B 5/0476 |
| | | | | 600/544 |
| 2012/0172744 A1* | 7/2012 | Kato | .............. | A61B 5/0478 |
| | | | | 600/544 |
| 2012/0177233 A1* | 7/2012 | Kidmose | ............ | A61B 5/04845 |
| | | | | 381/314 |
| 2013/0343585 A1* | 12/2013 | Bennett | ............ | H04R 25/554 |
| | | | | 381/315 |

\* cited by examiner

CONFIGURABLE HEARING INSTRUMENT

CROSS REFERENCE TO RELATED APPLICATIONS

This nonprovisional application claims the benefit of U.S. Provisional Application No. 61/737,133 filed on Dec. 12, 2012 and to patent application Ser. No. 12/197,265.7 filed in Europe, on Dec. 14, 2012. The entire contents of all of the above applications is hereby incorporated by reference.

BACKGROUND

Technical Field

The present invention relates to hearing instruments and particularly to configuration of a hearing instrument based on a mental state of a user. The invention specifically relates to a method for configuring one or more settings of the hearing instrument in response to detection of a particular mental state of the user wearing the hearing instrument.

Related Art

Hearing instruments, such as hearing aids, are electroacoustic devices often used for enhancing sound by ways of amplification and modulation. A hearing instrument gathers sound from surroundings, amplifies the sound and directs the sound to ear canals of the user wearing the hearing instrument. For example, in case of a hearing impaired person, a hearing instrument may be configured to amplify sound coming from a frontal direction and cancel noise generated from all other audio signals, such that clear sound is perceived by the hearing impaired person, wearing the hearing instrument. The amplification and/or modulation are typically performed based upon a hearing profile of the hearing impaired person.

Conventionally, hearing instruments are fitted in a user's ear in an in the ear (ITE) configuration, a behind the ear (BTE) configuration, an in the canal (ITC) configuration, etc. In some cases, when the user is in a relaxation state, the user usually tends to either remove the hearing instrument from the ear, or switch off the hearing instrument such that no sound reaches the user in the relaxation state. However, in such cases, the user may not even hear normal sounds that the user otherwise wishes to hear, for example, another person speaking with the user, ringing of a telephone, a door bell, etc., sounds that may signal emergency, and the like. In addition, the user may also face problems if the hearing instrument is misplaced or permanently lost. Further, some types of hearing instruments may be difficult to repeatedly remove and put on.

User configurable hearing instruments are known in the art. These hearing instruments are configured by a user according to particular needs of the user. The user can program the configurable hearing instrument using a computing device. Once the configuration is complete, the hearing instrument may work according to the configured settings. However, the user may require different types of configurations of the hearing instruments for different needs. For example, a user may want to have a decibel level of the sound, of the hearing instrument, automatically adjusted based on a particular mental state of the user. However, to change the settings repeatedly may be cumbersome for the user.

U.S. Pat. No. 6,330,339 discloses an invention intended to reduce the power consumption of a hearing aid chip by taking into account the users behavior, e.g. to reduce power if the hearing aid user is sleeping, in motion (accelerators) or if it is detected that the hearing aid user does not wear them, or if a time clock says that it is night, and thereby power could be reduced (by changing to various power saving modes).

It is an object of the present invention to provide a hearing instrument without the above disadvantages. It is a further object to provide a method for operating the hearing instrument which allows the hearing instrument to operate without the above disadvantages.

SUMMARY

As used herein, the singular forms "a," "an," and "the" are intended to include the plural forms as well (i.e. to have the meaning of "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements maybe present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

In an embodiment of the invention, a system comprising one or more electroencephalography (EEG) electrodes, a detector and a controller has been disclosed. The one or more EEG electrodes are disposed on the scalp of a user to measure brain wave signals of the user. The detector detects whether the user is in a relaxation state, based on the measured brain wave signals. The controller sets the hearing instrument to a relaxation mode setting in response to detection of the mental state of the user.

In an embodiment, the EEG electrodes are disposed on a surface of the hearing instrument. In another embodiment, the EEG electrodes are located outside of the hearing instrument and communicatively coupled to the hearing instrument. In an embodiment of the invention, at least one, such as a multitude, e.g. a majority or all of the (EEG) electrodes are implanted in the user's hear, e.g. in connection with a cochlear implant hearing device or with a partially implanted bone conducting hearing device.

The detecting unit is further configured to detect an active state of the user based on the measured brain wave signals. In response to detection of the active state of the user, the controller is further configured to set the hearing instrument to an active mode setting. The controller is further configured to set the hearing instrument to the active mode setting in response to a user action.

The relaxation mode setting comprises at least a reduced gain setting and/or a low pass filter setting.

In another embodiment of the present invention, a method for operating a hearing instrument has been disclosed. The method comprises using one or more electrodes to measure brain wave signals of a user wearing the hearing instrument. The method further comprises analyzing the measured brain wave signals to detect a relaxation state of the user and configuring one or more settings of the hearing instrument in response to detecting the relaxation state of the user.

In an example, the brain wave signals are measured using one of electroencephalography (EEG) and magnetoencephalography (MEG).

The analyzing further comprises detecting an alpha activity of the user. Alpha activity or alpha waves refer to brain waves (e.g. detected by EEG or MEG) during relaxation (in an awake state) with closed eyes. Alpha activity is reduced during sleep or half-sleep or when eyes are open.

In yet another embodiment of the present invention a hearing instrument is disclosed. The hearing instrument comprises one or more electroencephalography electrodes disposed on a scalp of a user to measure brain wave signals of the user wearing the hearing instrument. The hearing instrument further includes a detecting unit configured to detect a relaxation state of the user based upon the measured brain wave signals and a controller configured to set the hearing instrument to a relaxation mode setting in response to the detection of the relaxation state of the user.

The hearing instrument is one of a in the ear hearing instrument or behind the ear hearing instrument, according to one embodiment.

In an embodiment, the hearing instrument work in full power consumption all the time.

In the present context, a "hearing instrument" refers to a device, such as e.g. a hearing aid, a listening device or an active ear-protection device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A "hearing instrument" further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve and/or to the auditory cortex of the user.

A hearing instrument may be configured to be worn in any known way, e.g. as a unit arranged behind the ear with a tube leading air-borne acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. A hearing instrument may comprise a single unit or several units communicating electronically with each other.

More generally, a hearing instrument comprises an input transducer for receiving an acoustic signal from a user's surroundings and providing a corresponding input audio signal and/or a receiver for electronically receiving an input audio signal, a signal processing circuit for processing the input audio signal and an output means for providing an audible signal to the user in dependence on the processed audio signal. Some hearing instruments may comprise multiple input transducers, e.g. for providing direction-dependent audio signal processing. In some hearing instruments, the receiver may be a wireless receiver. In some hearing instruments, the receiver may be e.g. an input amplifier for receiving a wired signal. In some hearing instruments, an amplifier may constitute the signal processing circuit. In some hearing instruments, the output means may comprise an output transducer, such as e.g. a loudspeaker for providing an air-borne acoustic signal or a vibrator for providing a structure-borne or liquid-borne acoustic signal. In some hearing instruments, the output means may comprise one or more output electrodes for providing electric signals.

In some hearing instruments, the vibrator may be adapted to provide a structure-borne acoustic signal transcutaneously or percutaneously to the skull bone. In some hearing instruments, the vibrator may be implanted in the middle ear and/or in the inner ear. In some hearing instruments, the vibrator may be adapted to provide a structure-borne acoustic signal to a middle-ear bone and/or to the cochlea. In some hearing instruments, the vibrator may be adapted to provide a liquid-borne acoustic signal in the cochlear liquid, e.g. through the oval window. In some hearing instruments, the output electrodes may be implanted in the cochlea or on the inside of the skull bone and may be adapted to provide the electric signals to the hair cells of the cochlea, to one or more hearing nerves and/or to the auditory cortex.

A "hearing system" refers to a system comprising one or two hearing instruments, and a "binaural hearing system" refers to a system comprising one or two hearing instruments and being adapted to cooperatively provide audible signals to both of the user's ears. Hearing systems or binaural hearing systems may further comprise "auxiliary devices", which communicate with the hearing instruments and affect and/or benefit from the function of the hearing instruments. Auxiliary devices may be e.g. remote controls, remote microphones, audio gateway devices, mobile phones, public-address systems, car audio systems or music players. Hearing instruments, hearing systems or binaural hearing systems may e.g. be used for compensating for a hearing-impaired person's loss of hearing capability, augmenting or protecting a normal-hearing person's hearing capability and/or conveying electronic audio signals to a person.

BRIEF DESCRIPTION OF THE DRAWINGS

The figures are schematic and simplified for clarity, and they just show details which are essential to the understanding of the invention, while other details are left out. Throughout, the same reference numerals are used for identical or corresponding parts.

Further scope of applicability of the present invention will become apparent from the detailed description given hereinafter. However, it should be understood that the detailed description and specific examples, while indicating preferred embodiments of the invention, are given by way of illustration only, since various changes and modifications within the scope of the invention will become apparent to those skilled in the art from this detailed description.

DETAILED DESCRIPTION

Figure 1:
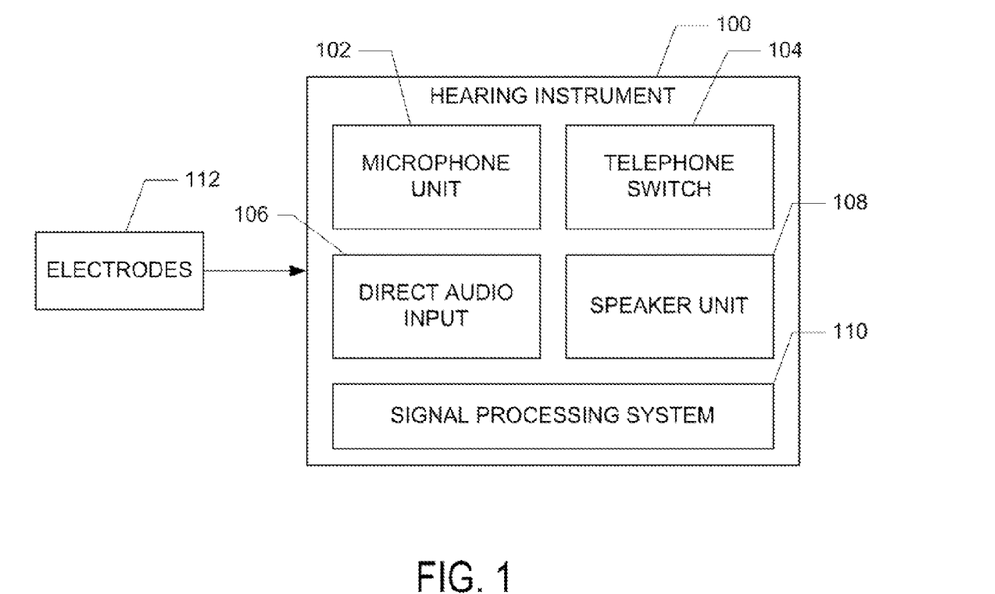
FIG. 1 illustrates an exemplary hearing instrument, in accordance with an exemplary embodiment of the present invention.

FIG. 1 illustrates an exemplary hearing instrument 100. The hearing instrument 100 includes one or more components for processing signals received from a nearby environment of a user wearing the hearing instrument 100. The one or more components include one or more of a microphone unit 102, a telephone switch 104, a direct audio input 106, a speaker unit 108, and a signal processing system 110. In an example, the hearing instrument 100 may be a digital hearing instrument such that signals received by the hearing instrument 100 are converted to a digital format for further processing.

The microphone unit 102 includes one or more microphones (not shown) for allowing the user to perceive clear and uninterrupted sound from a vicinity of the user. In an embodiment, the microphone unit 102 may be directional such that the microphone unit 102 amplifies sound coming from a particular direction and attenuate sounds coming from other directions. For example, the microphone unit 102 may amplify sounds coming from a frontal direction of the user and attenuate all other sounds. In an example implementation, the directionality may be achieved by directional microphones. In another example implementation, the microphone unit 102 may include two or more omnidirectional microphone and the directionality may be achieved by processing the microphone signals of the omnidirectional microphones. One example of such a processing is beamforming. In another embodiment, the microphone unit 102 may include omnidirectional microphones. In a further embodiment, the microphone unit 102 may also include both directional and omnidirectional microphones. In an example, the directional microphones may allow user to perceive clear sounds in a noisy environment, while the omnidirectional microphones may allow the user to perceive clear sounds in a relatively quieter environment. The user may be able to switch between the omnidirectional and the directional microphones according to particular needs and hearing conditions. In an example, the user may switch between the microphones using a switch placed on the hearing instrument 100 (not shown). In another example, dynamic switching between the microphones may also be provided.

The telephone switch 104 may be configured to switch the hearing instrument 100 to a "T-coil" setting. The T-coil setting may configure the hearing instrument 100 to be connected to a telephone such that clear sound from the telephone reaches the user and other sounds in the vicinity of the user are filtered out. The telephone switch 104 may also be configured, in an example, to turn off the microphones such that unwanted sounds (such as "whistling" sounds) are eliminated.

The direct audio input 106 allows the user to plug in the hearing instrument 100 to a remote microphone or a frequency modulation (FM) assistive listening system or a mobile telephone (e.g. a CellPhone). For example, the user may plug in the hearing instrument 100 to an external media player using the direct audio input 106.

The speaker unit 108 of the hearing instrument 100 includes one or more loudspeakers (not shown) for reproducing sound received by the hearing instrument 100. The one or more loudspeakers may be miniature neodymium magnet speakers. The speaker unit 108 may be located in a housing designed to fit snugly in the ear or the ear canal of the user.

The hearing instrument 100 also includes a signal processing system 110 for performing various signal processing tasks within the hearing instrument 100. Examples of the signal processing tasks are, without limitation, dynamic range compression, automatic gain control, beamforming, acoustic noise reduction, feedback suppression, and the like.

In one embodiment, the signal processing system 110 may also process signals received from one or more electrodes 112 (collectively referred to as electrodes 112) communicatively coupled to the hearing instrument 100 via a wireless or wired connection. In an embodiment, the signal processing system 110 may be configured to process brain wave signals of the user measured by the electrodes 112 to detect a mental state of the user. A "mental state" as used herein, refers to whether the user is relaxing, mentally active, excited, etc. For every mental state, brain wave signals may show activity in a corresponding frequency range. For example, the brain wave signals may show activity in an alpha frequency range (about 8-12 Hz.) when the user is in a relaxation state. In another example, the brain wave signals may show activity in a beta frequency range (about 13-30 Hz.) when the user is in an active state (i.e. alert or concentrating). The signal processing system 110 processes these brain wave signals to detect the mental state of the user and control one or more settings of the hearing instrument 100, based on the detected mental state of the user. The signal processing system 110 may include one or more processing components (not shown) for processing the brain wave signals measured by the electrodes 112. The processing components may include, without limitation, filters, analog to digital converters, noise reduction circuits, direct current blockers, and the like. The signal processing system 110 may thus receive the brain wave signals from the electrodes 112 and detect a mental state of the user by processing the received brain wave signals. FIG. 1 depicts the processing components for processing the brain wave signals to detect the mental state of the user as being integrated with the signal processing system 110, however, in an alternate embodiment, the processing components may be independent of the signal processing system 110 and be communicatively coupled to the hearing instrument 100 through a wired or a wireless connection.

The electrodes 112 are configured to measure and record brain wave signals of the user and transmit the measured signals to the signal processing system 110. In an embodiment, the electrodes 112 may be electroencephalography (EEG) electrodes or magnetoencephalography (MEG) electrodes. The electrodes 112, in an example, may be located on inner and outer surfaces of the hearing instrument 100 (cf. e.g. In another example, the electrodes 112 may be located directly on the scalp of the user and communicatively coupled to the hearing instrument 100 through a wired or a wireless connection. For example, the electrodes 112 may be communicatively coupled to the hearing instrument 100 via a Bluetooth® connection or a near-field magnetic induction (NFMI) communication connection. Various arrangements of the electrodes 112 with respect to the hearing instrument 100 are explained in detail in FIG. 2. In other embodiments, the electrodes 112 may be implanted in the head of the user.

Figures 2, 2A, 2B:
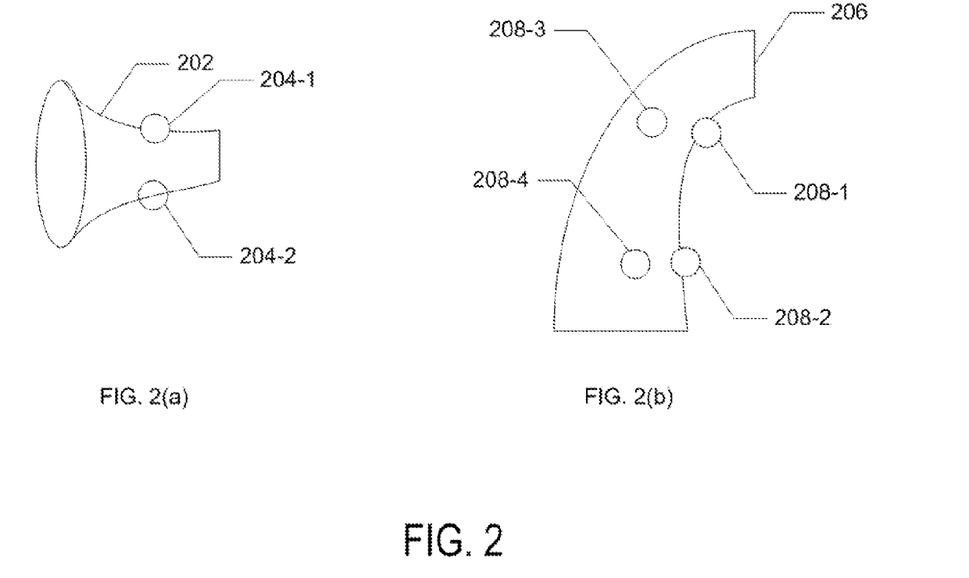
FIG. 2(a) illustrates an in the ear configuration of the hearing instrument, in accordance with an exemplary embodiment of the present invention.
FIG. 2(b) illustrates a behind the ear configuration of the hearing instrument, in accordance with an exemplary embodiment of the present invention.

FIG. 2 depicts various arrangements of one or more EEG electrodes on the hearing instrument 100 according to the invention.

FIG. 2(a) shows an 'in the ear' (ITE) part 202 of the hearing instrument 100 (shown in FIG. 1). In an embodiment, the ITE part 202 constitutes the hearing instrument 100. The ITE part 202 is adapted for being located fully or partially in the ear canal of the user. In one example, the ITE part 202 includes two EEG electrodes 204-1 and 204-2 (collectively referred to as electrodes 204) located on (or extending from) a surface of the ITE part 202. The ITE part 202 includes a mold (not shown) that may be adapted to a particular user's ear canal for fitting the ITE part 202. The mold, in an example, may be made of a form stable plastic material by an injection molding process or formed by a rapid prototyping process, e.g. a numerically controlled laser cutting process.

The ITE part 202 of the hearing instrument 100 fits in an outer ear bowl ('concha') of the user's ear. In an example, the ITE part 202 may be custom-made for different users to fit each user's ear. For fitting the ITE part 202 in the user's ear, a physical impression of the mold may be taken and scanned by a computer aided design (CAD) system, resulting in a three-dimensional model of the ear. A major characteristic associated with an ITE part is that the ITE part is tightly fitted to the ear canal. Thus, EEG electrodes 204 on the surface (or extending from the surface) of the ITE part 202 contacting walls of the ear canal may be well suited for forming an electrical contact to the body of the user. The ITE part 202 may alternatively be configured to be inserted completely in the ear canal of the user, e.g. as a so-called Completely-In-the-Canal (CIC) instrument.

FIG. 2(*b*) shows another embodiment of the (part of the) hearing instrument 100 according to the present invention. As depicted, a 'behind the ear' (BTE) part 206 of the hearing instrument 100 is adapted for being located behind the ear (e.g. pinna) of the user. In one example, the BTE part 206 includes four EEG electrodes 208-1 . . . 208-4 (collectively referred to as EEG electrodes 208) located on a surface of the BTE part 206, though any number of electrodes may be used. The EEG electrodes 208-1 and 208-2 (depicted by dotted circles) are located on a face of the BTE part 206, in a way that these EEG electrodes are supported by a ridge where the ear is attached to the scalp of the user. The other two EEG electrodes 208-3 and 208-4 (depicted by solid circles) are located on the face of the BTE part 206, such that these EEG electrodes are being supported directly by the scalp of the user.

The EEG electrodes 208 (or EEG electrodes 204 in case of ITE part 202) are specifically adapted for picking up brain wave signals from the user related to a direct measure of a mental state of the user. In an example, the EEG electrodes 208 (or electrodes 204) may all serve a same purpose (e.g. measuring brain wave signals) or different purposes (e.g. three for measuring brain wave signals and one for measuring body temperature).

In an alternate embodiment, the hearing instrument 100 according to the invention includes one or more additional EEG electrodes (not shown) contributing to the direct measurement of the brain wave signals of the user, but not located on the surface of the hearing instrument 100. In such an embodiment, the one or more additional EEG electrodes may be adapted to be connected to the hearing instrument 100 by a wired or wireless connection between the one or more additional EEG electrodes and the ITE part 202 (in case of monaural hearing instruments) or two ITE parts (in case of binaural hearing instruments). The one or more additional EEG electrodes may comprise an electronic circuit for picking up the brain wave signals from the scalp of the user and transmitting the brain wave signals to the ITE part 202. The wired connection may run along (or form part of the) flexible support members for holding the additional EEG electrodes in place on the head of the user. The wireless communication may occur using Bluetooth® or other suitable communication scheme. Further, the one or more additional EEG electrodes may be located in a symmetry plane of the head of the user (e.g. as defined by the line of the nose of the user, the ears are located symmetrically about the plane) and e.g. constituting a reference terminal.

Electrodes located on a housing of an a ITE part of a hearing instrument is e.g. discussed in US2010196861A1.

Figure 3:
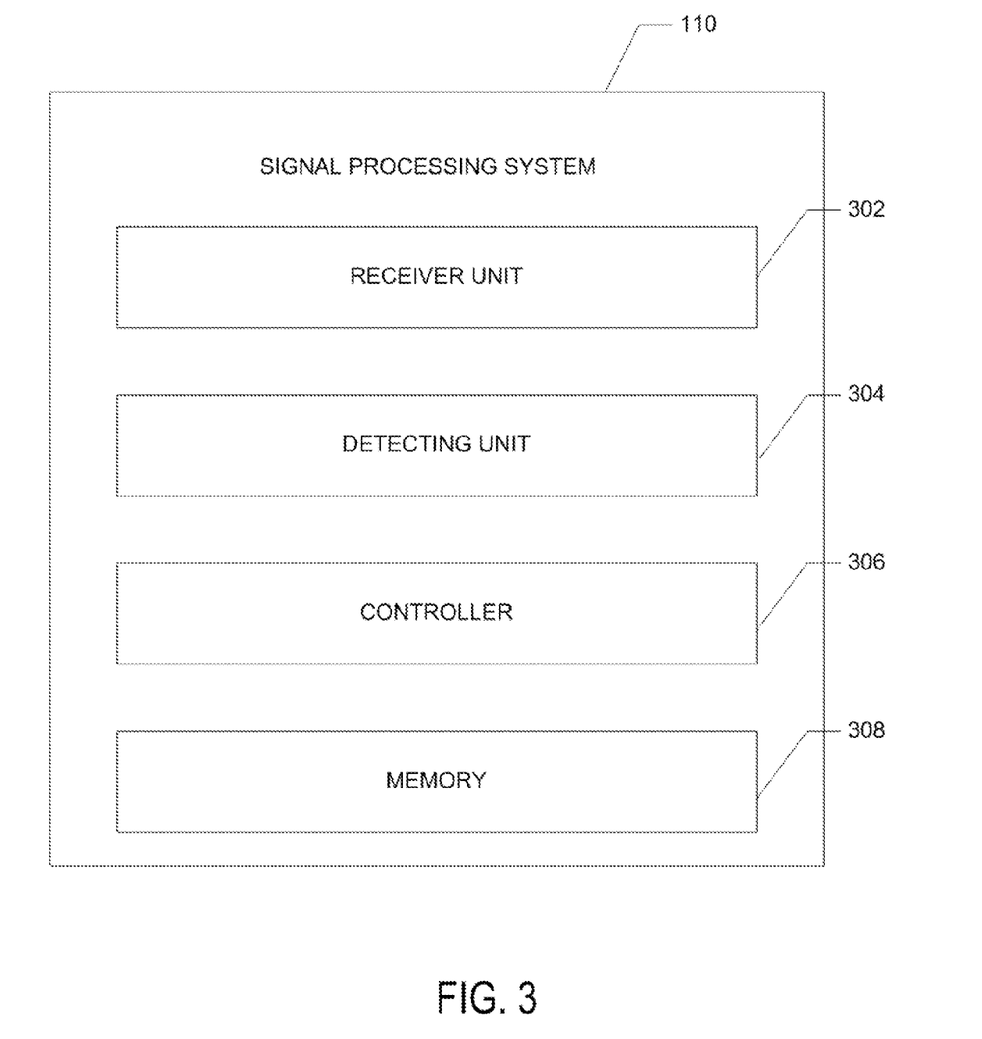
FIG. 3 illustrates various components of a signal processing system, in accordance with an exemplary embodiment of the present invention.

FIG. 3 illustrates components of the signal processing system 110 for processing the brain wave signals measured by the electrodes 112 and configuring one or more settings of the hearing instrument 100 (shown in FIG. 1) based on the processing of the brain wave signals, according to an embodiment. In various alternate embodiments, MEG electrodes may also be used. Further, FIG. 3 is described with reference to the signal processing system 110 being configured to detect a relaxation state of the user and configure the hearing instrument 100 for the relaxation state of the user. In such an embodiment, the EEG electrodes 112 are configured to measure the brain wave signals of the user and transmit these signals to the signal processing system 110. The signal processing system 110 may detect an alpha activity of the user (i.e. corresponding to the relaxation state of the user) by determining whether the signals lie in the alpha frequency range and set the hearing instrument 100 to a relaxation mode setting if it is detected that the majority of the signals received from the EEG electrodes 112 lie in the alpha frequency range. In various alternate embodiments, the signal processing system 110 may also be configured to detect other mental states of the user and configure the hearing instrument 100 accordingly.

Referring back to FIG. 3, the signal processing system 110 includes a (brain signal) receiver unit 302, a detecting unit 304, a controller 308, and a memory 310.

The receiving unit 302 is configured to receive the brain wave signals from the electrodes 112. The receiving unit 302 may have a set of receivers, such that the signals are captured by the signal processing system 110 using the receiving unit 302. In an example implementation, the receiving unit 302 may have a separate receiver for each electrode of the electrodes 112. The receiving unit 302 may also include an amplifier circuit for each receiver, receiving the output signal of the corresponding receiver, configured to amplify and modulate the received signals so as to increase the Signal to Noise Ratio (SNR) of the brain wave signals. The receiving unit 302 may further include one or more analog-to-digital converters, sampling circuits, etc. to convert the received brain wave signals to digital form.

The detecting unit 304 is configured to process the signals received by the receiving unit 302 and analyze the received signals for detecting a relaxation state of the user. The detecting unit 304 includes one or more processing components (not shown), for processing the received signals. The one or more processing components include, without limitation, low pass filters, band pass filters, direct current (DC) blockers, comparators, and the like. The one or more processing components may work collectively or individually for processing the signals such that these signals are analyzed for detection of a mental state of the user.

The controller 306 receives commands from the detecting unit 304 when it is detected that the user is in the relaxation state. In an embodiment, the controller 306 may set the hearing instrument 100 to the relaxation mode setting, when the controller 306 receives command signals, regarding the relaxation state of the user, from the detecting unit 304. The relaxation mode setting may correspond to settings of the hearing instrument 100 when the user is in the relaxation state. The relaxation mode settings may be pre-configured by the user within the memory 308 of the signal processing system 110. In an example, the controller 306 may process one or more signals for switching the hearing instrument 100 to the relaxation mode settings. For example, the controller 306 may reduce the overall gain applied to microphone signals. In one example, the controller 306 may filter the microphone signals using a low pass filter. In an example, the controller 306 may reduce the overall gain applied to the microphone signals and filter the microphone signals using a low pass filter. A person skilled in the art will recognize other examples of changing the settings of the hearing instrument 100 when the relaxation state is detected. One example may be to apply a tinnitus sequence configured to mask a perception of annoying sound signals (tinnitus) in a user's brain.

In an embodiment, the controller 306 may also be configured to set the hearing instrument 100 to an active mode setting corresponding to an active state of the user. The active state of the user may correspond to a mental state of the user, when the user is mentally active. In one example, the controller 306 may automatically set the hearing instrument 100 to the active mode setting when the active state of the user is detected. In one exemplary implementation, the detecting unit 304 may be further configured to automatically detect the active state too and send a command to the controller 306 in response to detecting the active state. In another embodiment, the controller 306 may set the hearing instrument 100 to the active mode setting in response to a user action, such as pressing of a knob or a switch located on the hearing instrument 100 (or operating a user interface, e.g. a touch sensitive screen of a remote control device, e.g. a SmartPhone).

The memory 308 is storage medium for storing one or more parameters associated with the hearing instrument 100. The one or more parameters may include, without limitation, operational parameters, threshold values, time constants, user settings for the hearing instrument 100, hearing instrument specifications, and the like. The memory 308, in an example, may be a read-only memory (ROM), a random access memory (RAM) or cache memory. The memory 308 may be programmable through a computing unit for configuring the hearing instrument 100 for a user's need. The memory 308 may also be re-programmable for switching between different settings of the hearing instrument 100.

Figure 4:
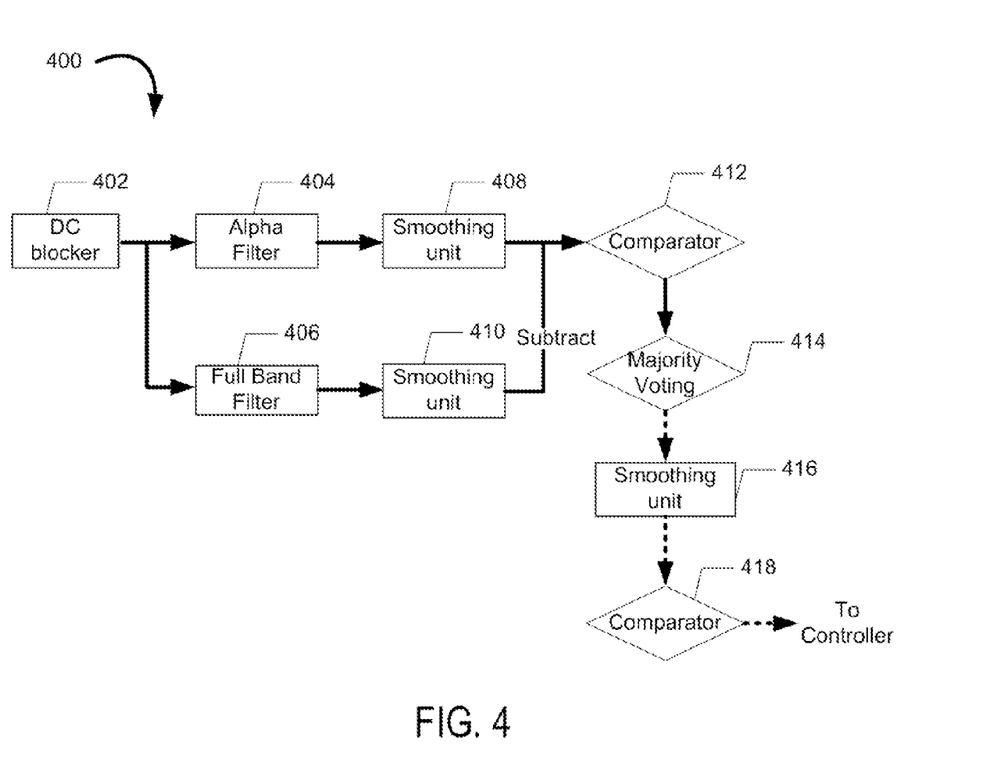
FIG. 4 illustrates a functional block diagram for operating the signal processing system, in accordance with an exemplary embodiment of the present invention.

FIG. 4 illustrates a functional block diagram 400 depicting working of the detecting unit 304 for detecting a relaxation state of the user wearing the hearing instrument 100, in accordance with an embodiment of the present invention.

The brain wave signals are transmitted from the receiving unit 302 to the detecting unit 304. The detecting unit 304 processes the received signals for detecting the mental state of the user so as to give commands to the controller 306 for changing one or more settings of the hearing instrument 100. Referring back to FIG. 4, solid arrow lines depict multiple channels of the signals that are being processed simultaneously, with each channel corresponding to the brain wave signals received from one electrode. Thus, if three electrodes are present, the number of channels will be three, and so on. The dotted arrow lines depict a single channel processing of the signals.

As depicted in FIG. 4, the signals from the receiving unit 302 (shown in FIG. 3) are fed into a direct current (DC) blocker 402. The signals from the receiving unit 302 may be converted to digital signals by means of sampling and then divided into blocks of samples before passing to the DC blocker 402. In an example implementation, blocks of 64 samples may be used, though any other suitable block length may be used. Further, the blocks may be overlapping or non-overlapping. The DC blocker 402 may e.g. be a passive analog circuit. In another example, the DC blocker may be implemented in a digital manner. The DC blocker 402 is configured to increase the SNR of the signals by blocking the DC. The DC blocker 402 may be implemented as a high pass filter configured, for example, to allow signals with frequencies above 3 Hertz (Hz) to pass through and to block all other signals.

The DC-blocked signals may be passed through an alpha filter 404 and a full band filter 406. The alpha filter 404 may be configured to band-pass filter the signals in a frequency band of, for example, about 8 Hz to about 12 Hz, i.e. in an alpha frequency band. The full band filter 406 may be a band stop filter configured to block the signals in a frequency band of, for example, about 3 Hz to about 24 Hz. Such an arrangement of the alpha filter 304 and the full band filter 406 may ensure that the signal frequencies passing through the alpha filter 404 do not pass the full band filter. The alpha filter 404 and the full band filter 406 may be configurable by setting and/or changing one or more parameters. Examples of the one or more parameters may include frequency bands, attenuation factor, ripple factor, and the like. The frequency bands presented herein are merely exemplary for detecting the relaxation state of the user. Different frequency bands and other filter parameter values may be used if the detecting unit 304 is configured for detecting other mental states of the user. Values of the one or more parameters are saved, in an example, in the memory 306. In another example, the one or more parameters may also be stored in an external database coupled to the signal processing system 110. The DC blocker 402 and the full band filter 406 provide the advantage of increasing robustness to the signal processing system 110. In an exemplary implementation, the signals may be directly processed without feeding these signals into the DC blocker 402 and the full band filter 406.

The output signals from the alpha filter 404 are smoothed in the smoothing unit 408. Similarly, the output signals from the full band filter 406 are smoothed in the smoothing unit 410. The smoothing may be performed using root means square (RMS) smoothing technique specified in the following equation:

$$y[n] = \sqrt{\sum_{m=0}^{M-1} (x[n-m])^2}$$

In the above equation, y[n] denotes the output of the RMS smoothing and x[n] denotes an input signal. Running sample index of the smoothing is denoted by n and duration of the smoothing measured in whole samples is denoted by m. For the smoothing unit 408, the input signal x[n] is the signal filtered by the alpha filter 404. Similarly, for the smoothing unit 410, the input signal x[n] is the signal filtered by the full band filter 406. In an example implementation, the time constant for RMS smoothing may be 800 ms. The RMS smoothed signals may be represented in decibels (dB).

Once the signals have undergone RMS smoothing, the smoothed signals from the smoothing unit 410 are subtracted from the smoothed signals from the smoothing unit 408. Subtracting the signals represented in dB corresponds to dividing the original signals and thus provides an automatic calibration of the system. The signals may be subtracted from each other in order to improve robustness against errors in the processing. The errors in the processing of signals may occur due to variations resulted from degree of contact of the electrodes 112 with the scalp of the user, time of measurement of the EEG signals, and the like. Further, the error may also occur due to variations between different users. Therefore, the need of adapting the signal processing to a threshold value is lessened and more accurate processing is obtained.

Output signals of the subtraction are passed to a comparator 412. The comparator 412 compares the output signal in each channel to a channel specific threshold value. The result of the comparison represents whether the user is in the relaxation state. For example, when the signal after the subtraction for a given channel is greater than the channel-specific threshold for that channel, the brain wave signal measurements for that channel indicate that the user may be in the relaxation state. In an example, the channel specific threshold may be obtained from the memory 308.

The results of the channel-wise comparison may be combined to give a single output representing whether the user in the relaxation state. In an example implementation, the combining may be done using majority voting technique, though other suitable techniques may also be used. The majority voting may be done by block 414. The majority voting may calculate number of channels that contain signals above a decision threshold in the alpha wave frequency range. If more than a majority of the total number of channels have signals above the decision threshold in the alpha wave frequency range, the combined signal may be set to "one". Otherwise, the combined signal may be set to "zero". The combined signal may then be smoothed using a smoothing unit 416. The smoothing is performed to improve robustness of the decision against time-dependent variations in individual channels leading to rapid switching between "one" (indicating that the user is in the relaxation state) and "zero" (indicating that the user is not in the relaxation state). In an example implementation, a time constant of 4500 ms may be used in the smoothing unit 416. The smoothened combined signal is compared with a detection threshold by a comparator 418. If the smoothed signal is above the detection threshold, it is determined that the user is in the relaxation state, and a command signal may be sent from the detecting unit 304 to the controller 306 (shown in FIG. 3). In an example, the detection threshold may be obtained from the memory 308 of the signal processing system 110.

The controller 306 is configured to set the hearing instrument 100 to the relaxation mode setting in response to the command signals received from the detecting unit 304. In an example, the user may configure separate settings for a relaxation state. For example, a reduced-gain and/or a low pass filtering of the sound may be set by the user such that in the relaxation state, the user may obtain a damping of sounds reaching the user's ear. Such a setting may invoke an atmosphere of the hearing instrument 100 "being off" without the need of removing the hearing instrument 100 from the user's ear. Thus, the need of repeatedly removing and putting on the hearing instrument 100 is eliminated. Further, clear and comfortable listening of sounds may be obtained.

Figure 5:
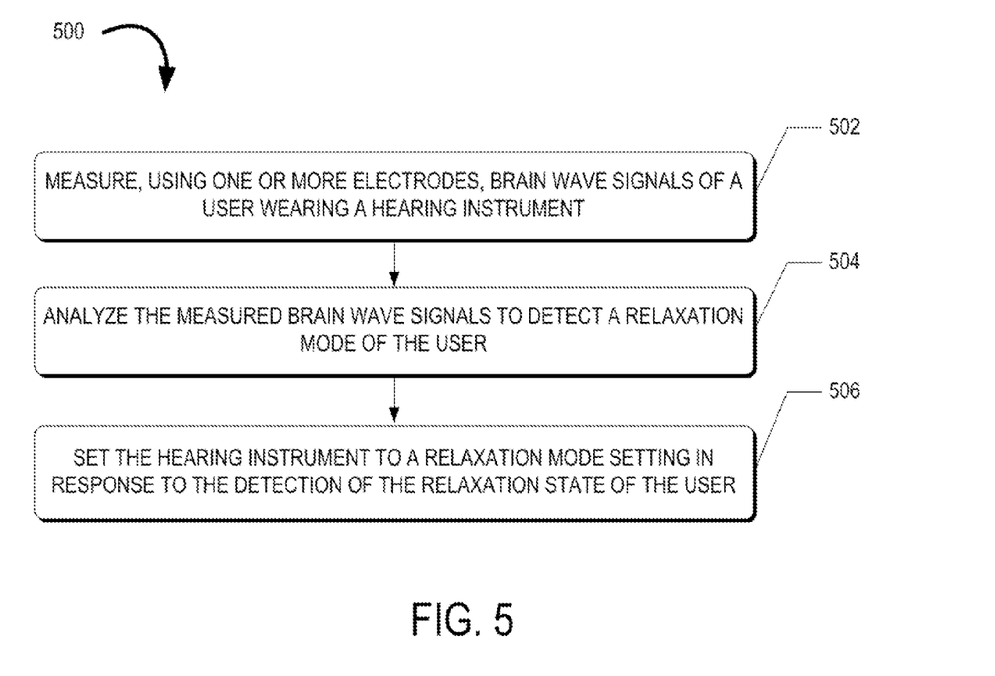
FIG. 5 illustrates a method for operating the hearing instrument, in accordance with an exemplary embodiment of the present invention.

FIG. 5 illustrates a process flow 500 for operating the hearing instrument 100 according to an embodiment of the present invention.

The process flow 500 starts at step 502, where one or more electrodes, such as the EEG electrodes 204 or the EEG electrodes 208, measure brain wave signals of a user wearing the hearing instrument 100.

At step 504, the measured brain wave signals are analysed to detect a relaxation state of the user. The brain wave signals may be analysed, for example, by the detecting unit 304.

At step 506, the hearing instrument 100 is set to the relaxation mode setting in response to the detection of the relaxation state of the user. The relaxation mode setting may include a low pass filter setting, a reduced gain setting, and the like. The hearing instrument 100 may be switched to the relaxation mode setting by the controller 306.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims. The features of disclosed embodiments may be combined arbitrarily.

The invention claimed is:

1. A signal processing system, comprising:
one or more electroencephalography electrodes configured to be disposed on a scalp and/or in an ear canal and/or implanted in the head of a user to measure brain wave signals of the user wearing a hearing instrument;
a detecting unit configured to determine whether a majority of the measured brain wave signals of the user are in alpha frequency range; and
a controller configured to set the hearing instrument to a relaxation mode setting in response to the determination that the majority of the measured brain wave signals of the user are in the alpha frequency range.

2. The signal processing system of claim 1, wherein the one or more electrodes are disposed on a surface of the hearing instrument.

3. The signal processing system of claim 1, wherein the one or more electrodes are located outside of the hearing instrument and communicatively coupled to the hearing instrument.

4. The signal processing system of claim 1, wherein:
the detecting unit is further configured to detect an active state of the user, based on the measured brain wave signals; and
in response to detection of the active state of the user, the controller is further configured to set the hearing instrument to an active mode setting.

5. The signal processing system of claim 1, wherein the controller is further configured to set the hearing instrument to an active mode setting in response to a user action.

6. The signal processing system of claim 1, wherein the relaxation mode setting comprises at least a reduced gain setting and/or a low pass filter setting.

7. The signal processing system of claim 6, wherein the relaxation mode setting comprises a low pass filter setting.

8. The signal processing system according to claim 1, wherein the controller is further configured to generate a tinnitus masking sequence when the controller sets the hearing instrument to the relaxation mode setting.

9. A method for selecting a setting of a hearing instrument, the method comprising:
measuring, using one or more electrodes, brain wave signals of a user wearing a hearing instrument;
determining whether a majority of the measured brain wave signals of the user are in alpha frequency range; and setting the hearing instrument to a relaxation mode setting in response to the determination that the majority of the measured brain wave signals of the user are in the alpha frequency range.

10. The method of claim 9, wherein the brain wave signals are measured using one of electroencephalography and magnetoencephalography.

11. The method of claim 10, further comprising:
analyzing the measured brain wave signals to detect an active state of the user; and
set the hearing instrument to an active mode setting in response to the detection of the active state of the user.

12. The method of claim 11, further comprising:
setting the hearing instrument to the active mode setting in response to a user action.

13. The method of claim 10, wherein the relaxation mode setting comprises at least a reduced gain setting and/or a low pass filter setting.

14. The method of claim 13, wherein the relaxation mode setting comprises a low pass filter setting.

15. The method according to claim 9, further comprising:
generating a tinnitus masking sequence when the hearing instrument is set to the relaxation mode setting.

16. A hearing instrument, comprising:
one or more electroencephalography electrodes configured to be disposed on a scalp of a user to measure brain wave signals of the user wearing the hearing instrument;
a detecting unit configured to determine whether a majority of the measured brain wave signals of the user are in alpha frequency range; and
a controller configured to set the hearing instrument to a relaxation mode setting in response to the determination that the majority of the measured brain wave signals of the user are in the alpha frequency range.

17. The hearing instrument of claim 16, wherein the hearing instrument is one of a in the ear hearing instrument or behind the ear hearing instrument.

18. The hearing instrument of claim 16, wherein the relaxation mode setting comprises at least a reduced gain setting and/or a low pass filter setting.

19. The hearing instrument of claim 18, wherein the relaxation mode setting comprises a low pass filter setting.

20. The hearing instrument according to claim 16, wherein the controller is further configured to generate a tinnitus masking sequence when the controller sets the hearing instrument to the relaxation mode setting.

* * * * *